US010331849B2

(12) United States Patent
Burke et al.

(10) Patent No.: US 10,331,849 B2
(45) Date of Patent: Jun. 25, 2019

(54) SYSTEM AND METHOD FOR CONSTRUCTION OF INTERNAL CONTROLS FOR IMPROVED ACCURACY AND SENSITIVITY OF DNA TESTING

(71) Applicant: Echelon Diagnostics, Inc., Reno, NV (US)

(72) Inventors: John Burke, Reno, NV (US); Stephen Healy Sanders, Reno, NV (US)

(73) Assignee: ECHELON DIAGNOSTICS, INC., Reno, NV (US)

( * ) Notice: Subject to any disclaimer, the term of this patent is extended or adjusted under 35 U.S.C. 154(b) by 733 days.

(21) Appl. No.: 14/709,417

(22) Filed: May 11, 2015

(65) Prior Publication Data

US 2016/0335392 A1 Nov. 17, 2016

(51) Int. Cl.
*G16B 30/10* (2019.01)
*G06F 19/22* (2011.01)

(52) U.S. Cl.
CPC .................... *G06F 19/22* (2013.01)

(58) Field of Classification Search
CPC ....................................... G06F 19/22
See application file for complete search history.

(56) References Cited

U.S. PATENT DOCUMENTS

2013/0230916 A1* 9/2013 Namir ............... G06F 19/22
435/320.1

OTHER PUBLICATIONS

Sehnert et al., (Clinical Chemistry. 2011: 57(7);1042-1049) (Year: 2011).*

Fan et al. Sensitivity of Noninvasive Prenatal Detection of Fetal Aneuploidy from Maternal Plasma Using Shotgun Sequencing Is Limited Only by Counting Statistics PLOS one vol. 5, article e10439 (Year: 2010).*
Ehrich et al. Noninvasive detection of fetal trisomy 21 by sequencing of DNA in maternal blood: a study in a clinical setting American Journal of Obstetrics and Gynecology vol. 204 article 205.e1-11 (Year: 2011).*
Bianchi, Diana W., et al., "DNA Sequencing versus Standard Prenatal Aneuploidy Screening", "New England Journal of Medicine", 2014, pp. 799-808, vol. 370, No. 9, Publisher: Massachusetts Medical Society, Published in: DOI: 10.1056/NEJMoa1311037.
Sehnert, Amy J., et al., "Optimal Detection of Fetal Chromosomal Abnormalities by Massively Parallel DNA Sequencing of Cell-Free Fetal DNA from Maternal Blood", "Clinical Chemistry", 2011, pp. 1042-1049, vol. 57, No. 7, Publisher: American Association for Clinical Chemistry, Published in: DOI: 10.1373/clinchem.2011.165910.

* cited by examiner

*Primary Examiner* — John S Brusca
(74) *Attorney, Agent, or Firm* — Beusse Wolter Sanks & Maire

(57) ABSTRACT

Techniques for construction of internal controls for improved accuracy and sensitivity of DNA testing include obtaining first data and determining weights over real numbers for a normalization function in less than a day. The first data indicates a measured amount of reference sequences for nucleic acids from training samples. The reference sequences include a target, for which an abundance is indicative of a condition of interest, and covariates not correlated with the condition of interest. The normalization function involves a sum of abundances of the covariates, as internal controls, each multiplied by a corresponding one of the weights. The weights are determined based on minimizing variance of a Taylor expansion of a ratio of a measured amount of the target divided by a value of the normalization function evaluated with measured amounts of the covariates over a portion of the first data in which the condition is absent.

25 Claims, 6 Drawing Sheets

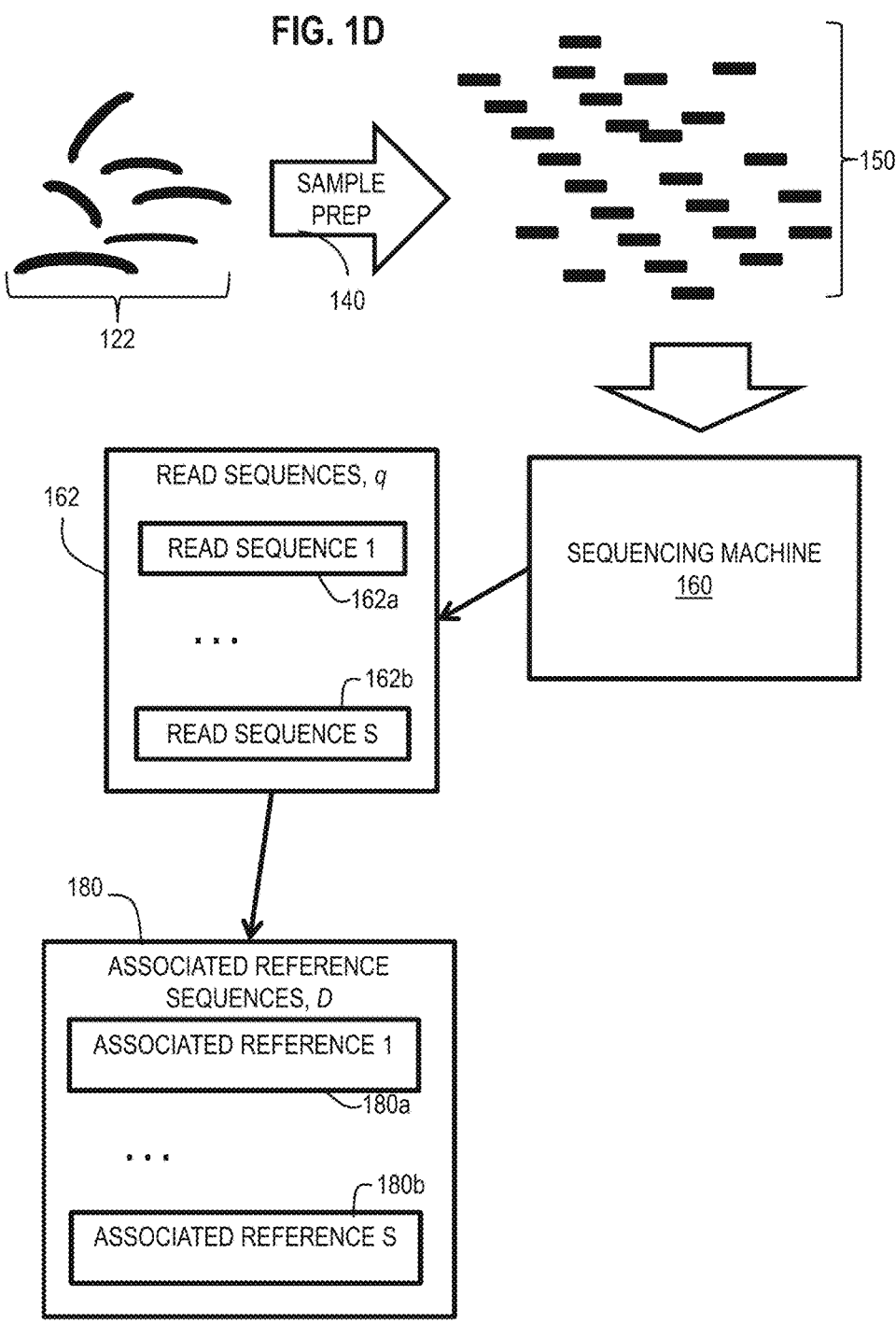

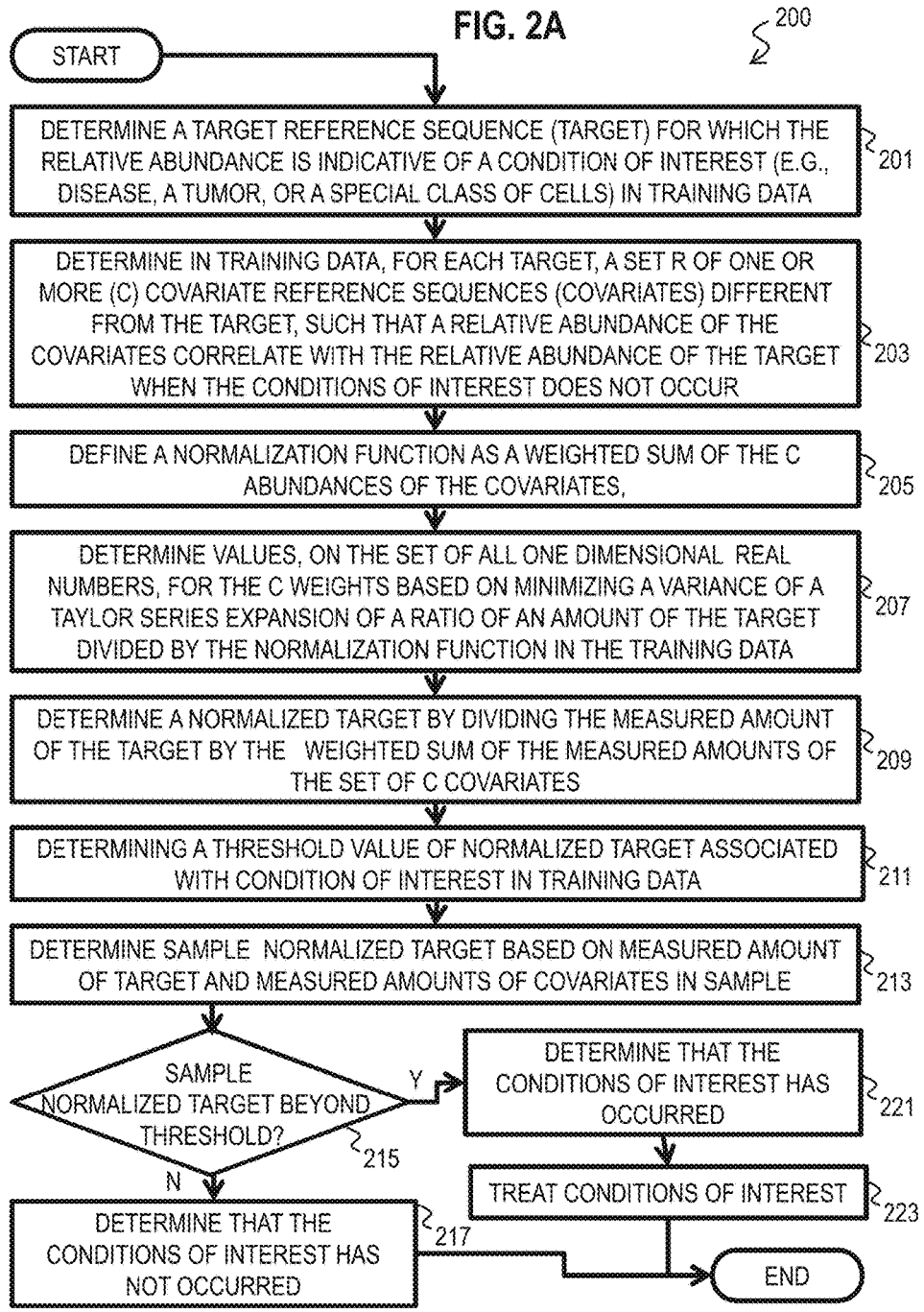

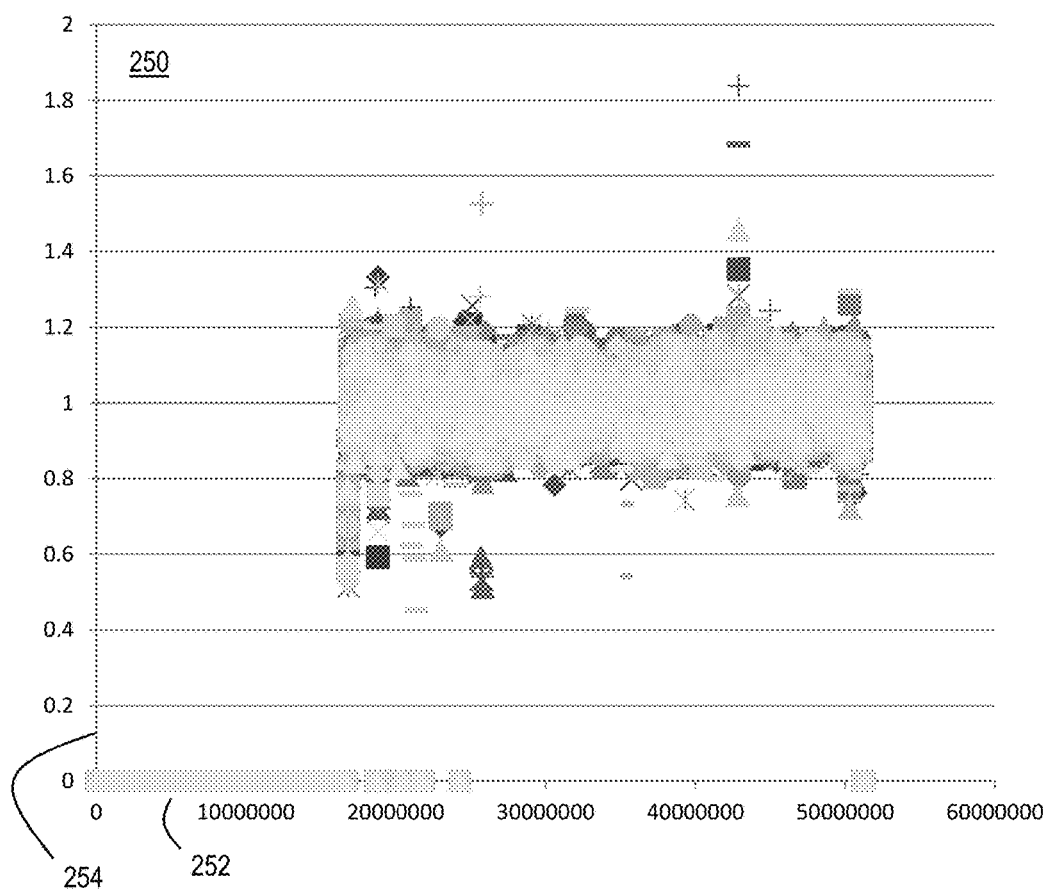

SYSTEM AND METHOD FOR CONSTRUCTION OF INTERNAL CONTROLS FOR IMPROVED ACCURACY AND SENSITIVITY OF DNA TESTING

BACKGROUND

Massively Parallel Sequencing (MPS) approaches such as those now in wide commercial use (Illumina/Solexa, Roche/454 Pyrosequencing, and ABI SOLiD) are attractive tools for sequencing. Typically, MPS methods can only obtain short read lengths (hundreds of base pairs, bp, also called nucleotides, nt, with Illumina platforms, to a maximum of 200-300 nt by 454 Pyrosequencing) but perform many thousands to millions of such short reads on the order of hours. Sanger methods, on the other hand, achieve longer read lengths of approximately 800 nt (typically 500-600 nt with non-enriched DNA) but take several times longer to do so.

While sequencing machines were originally created for the purposes of sequencing genomic DNA, they have since been put to a myriad of other uses. Considering a sequencer simply as a device for recording the count of specific DNA sequences, sequence census experiments utilize high-throughput sequencing to estimate abundances of "target sequences" (also called "reference sequences") for molecular biology and biomedical applications. Unusual populations of certain reference sequences can be diagnostic of disease.

To compare the DNA of the sequenced sample to its reference sequence, current methods are designed to find the corresponding part of that sequence for each read in the output sequencing data. This step is called aligning or mapping the reads against the reference sequence. Once this is done, one can look for one or more variations (e.g., a single nucleotide polymorphism, SNP, or a copy number variation, CNV, or a structural variation like presence/absence variation, PAV, or multiples or combinations thereof) within the sample. Aligning the read to the reference consumes a considerable amount of computing power.

For example, Sehnert et al 2011 and Biananchi et al 2014 describe methods to identify aneuploidy in a fetus from maternal blood samples, thus avoiding expensive and dangerous invasive procedures. Aneuploidy is a condition in which the number of chromosomes in the nucleus of a cell is not an exact multiple of the monoploid number of a particular species. An extra or missing chromosome is a common cause of genetic disorders including human birth defects. The fetal DNA in maternal blood is a very small portion of the sample (e.g., less than 10% and often as little as 0.5%) and the identification of its sequences is thus subject to systematic and random errors in the sample preparation, sequencing and alignment processes.

Similarly, cancerous tumors may have CNVs, PNVs, other structural mutations, or express different genes than the populations of normal cells in an individual. The tumor DNA in a patient tissue sample is a relatively small portion of the sample (e.g., less than 15% and sometimes as little as 0.5%) and the identification of its sequences is likewise subject to systematic bias and random errors in the sample preparation, sequencing and alignment processes.

SUMMARY

Techniques are provided for construction of internal controls for improved accuracy and sensitivity of DNA testing.

In a first set of embodiments, a method includes obtaining first data and determining, automatically on a processor, a set of one or more weights over real numbers for a normalization function. The first data indicates a measured amount of each of multiple reference sequences for nucleic acids from each of multiple training samples. The reference sequences include a target reference sequence and a set of one or more covariate reference sequences. A relative abundance of the target reference sequence compared to other reference sequences is indicative of a condition of interest. The set of one or more covariate reference sequences are different from the target reference sequence, and a relative abundance of each of the covariate reference sequences is not correlated with the condition of interest. A value, over real numbers, is determined for each weight of the set of one or more weights for the normalization function that involves a sum of relative abundances of the set of one or more covariate reference sequences, each relative abundance multiplied by a corresponding one of the set of one or more weights. The determination is based on minimizing a variance of a Taylor expansion of a ratio of a measured amount of the target reference sequence divided by a value of the normalization function evaluated with measured amounts of the set of one or more covariate reference sequences over a portion of the first data in which the condition of interest does not occur.

In some embodiments of the first set, the value over real numbers for each weight of the set of one or more weights is accomplished in about one day or less.

In some embodiments of the first set, the method further includes obtaining second data that indicates a measured amount of the target reference sequence and a measured amount of each of the covariate reference sequences in a clinical sample from a subject. The method also includes determining a normalized target value equal to a ratio of the measured amount of the target reference sequence in the second data divided by a value of the normalization function evaluated with measured amounts of the set of one or more covariate reference sequences over the second data. The method still further includes determining that the condition of interest has occurred in the subject if the normalized target value is beyond a threshold value.

In some of these latter embodiments, the clinical sample includes a component from blood of a pregnant female mammalian subject; each different reference sequence is a different entire chromosome of a species of the subject; and the condition of interest includes aneuploidy in a fetus carried by the subject.

In other sets of embodiments, a computer-readable medium, a system, or an apparatus is configured to cause an apparatus to perform one or more steps of the above methods.

Still other aspects, features, and advantages are readily apparent from the following detailed description, simply by illustrating a number of particular embodiments and implementations, including the best mode contemplated for carrying out the invention. Other embodiments are also capable of other and different features and advantages, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

Embodiments are illustrated by way of example, and not by way of limitation, in the figures of the accompanying drawings in which like reference numerals refer to similar elements and in which:

FIG. 1D is a block diagram that illustrates an example process to obtain reads from a sample and associate reads with reference sequences, according to an embodiment;

FIG. 2A is a flow chart that illustrates a method for forming and using internal controls to increase the accuracy and sensitivity of DNA testing, according to an embodiment;

FIG. 2B is a plot that illustrates example distribution of abundances of regions of a chromosome among thousands of samples in a training data for determining covariates as internal controls, according to an embodiment;

DETAILED DESCRIPTION

Figure 1A:
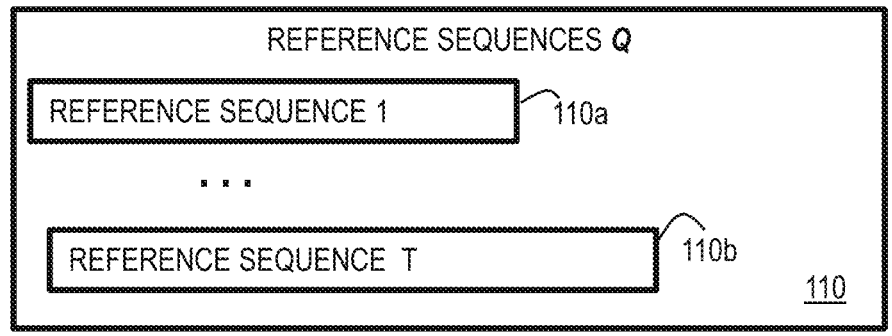
FIG. 1A through FIG. 1C are block diagrams that illustrate relative abundance of reference sequences in a sample.

A method and apparatus are described for construction of internal controls for improved accuracy and sensitivity of DNA testing. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 4.

Some embodiments of the invention are described below in the context of identifying aneuploidy in a fetus from a maternal blood sample. However, the invention is not limited to this context. In other embodiments, the nucleotide sequencing and internal control are used to detect other genetic defects, detect the presence of tumors (e.g., by analysis of circulating tumor DNA in blood), classify differences among different samples, or provide a census of expressed genes. In some embodiments, the method is applied to plant and animal screening for the identification of aneuploidy, chromosomal defects, as well as identification of translocations. The ability to detect signal present at low fraction of the total signal also is applicable to the surveillance and detection of unlicensed use of crop and seed germplasm. For example, in a bag of seed, only one out of several hundred seeds may contain protected inbred seed.

1. OVERVIEW

Deoxyribonucleic acid (DNA) is a, usually double-stranded, long molecule that is used by biological cells to encode other shorter molecules, such as proteins, used to build and control all living organisms. DNA is composed of repeating chemical units known as "nucleotides" or "bases." There are four bases: adenine, thymine, cytosine, and guanine, represented by the letters A, T, C and G, respectively. Adenine on one strand of DNA always binds to thymine on the other strand of DNA; and guanine on one strand always binds to cytosine on the other strand and such bonds are called base pairs. Any order of A, T, C and G is allowed on one strand, and that order determines the reverse complementary order on the other strand. The actual order determines the function of that portion of the DNA molecule. Information on a portion of one strand of DNA can be captured by ribonucleic acid (RNA) that also is composed of a chain of nucleotides in which uracil (U) replaces thymine (T). Determining the order, or sequence, of bases on one strand of DNA or RNA is called sequencing. A portion of length k bases of a strand is called a k-mer; and specific short k-mers are called oligonucleotides or oligomers or "oligos" for short.

Figure 1B:
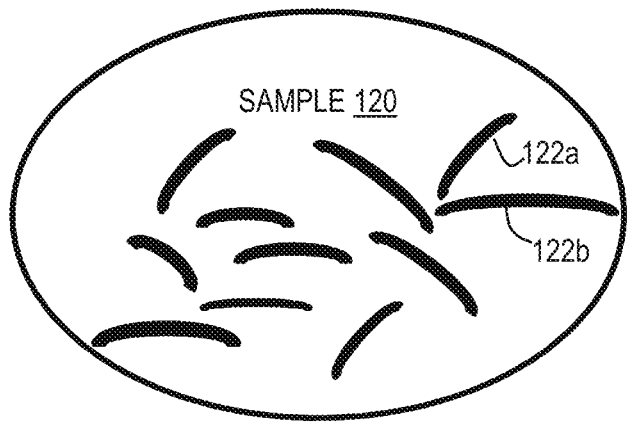
Figure 1C:
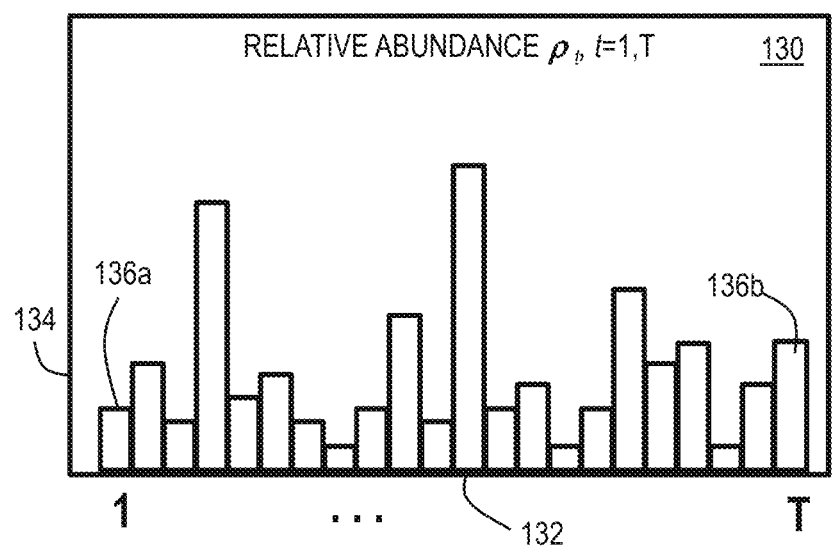

FIG. 1A through FIG. 1C are block diagrams that illustrate relative abundance of reference sequences in a sample. FIG. 1A is a block diagram that illustrates an example data structure 110 of C reference sequences Q, including field 110a holding data that indicates first reference sequence ($Q_1$), through field 110b holding the last (Tth) reference sequence ($Q_T$), among others indicated by ellipsis. An individual reference sequence is indicated by Qt, where t∈1, . . . , T. A reference sequence can refer to a normal (also called most common or consensus sequence or baseline or disease free sequence) or a SNP, CNV, PAV or other structural variation of the normal sequence.

FIG. 1B is a block diagram that represents an example sample 120 with multiple occurrences of nucleic acids, e.g., 122a, 122b (collectively referenced hereinafter as nucleic acids 122) each having one of the reference sequences. There may be several occurrences of a nucleic acid with one of the reference sequences and few or no occurrences of nucleic acids with another of the reference sequences. FIG. 1C is a bar graph 130 that illustrates example relative abundance data. The horizontal axis 132 indicates the reference sequences $Q_t$ {t=1, T}. The vertical axis 134 indicates relative number of nucleic acids in the sample (designated by the symbol ρ) with each reference, with a higher value indicating a greater abundance of the associated reference sequence. Graph 130 indicates that $Q_1$ occurs in the sample 120 with a relative abundance $\rho_1$ indicated by bar 136a, and $Q_T$ occurs in the sample 120 with a relative abundance $\rho_{TT}$ indicated by bar 136b. The abundance distribution is represented by $\rho=\rho_t$, {t=1, T}.

A problem is that ρ is not measured directly during sequencing experiments, but must be inferred by a large number S of sequencing reads (simply called reads, herein), represented by the symbol $q_s$ {s=1, S}, where each sequence of each read is short compared to a reference sequence $Q_t$.

FIG. 1D is a block diagram that illustrates an example process to obtain reads from a sample and associate reads with reference sequences, according to an embodiment. The nucleic acids 122 in a sample are prepared for the sequencer in a wide variety of ways known in the art, often by de-naturing to release the nucleic acids, fragmentation to allow the short reads to begin sequencing from anywhere within the nucleic acid having the reference sequence, to hybridization or replication or amplification or size selection, among others, or some combination, which collectively are referenced herein as sample preparation process 140. The resulting nucleic acids 150 are then sequenced with whatever bias or systematic variation are introduced by the sequencing process in sequencing machine 160. The reads $q_s$ {s=1, S} are recorded in a data structure 162 with a field holding data that represents each read sequence, such as field 162*a* for $q_1$ to field 162*b* for $q_S$, among others indicated by ellipsis.

If each read were uniquely found in one and only one reference sequence, then one of the T reference sequences $Q_t$ can be associated with each read, as indicated by the data structure 180 which associates with each read $q_s$ {i∈1, S} an associated reference sequence $D_s$, {s∈1, ..., S} where $D_s$=t {t∈1, ..., T}. Then a histogram of the distribution of the $D_s$ among the T references sequences could be used as an approximation of the abundance distribution ρ, or corrected for the known or inferred non-random sampling introduced by processes 140 and machine 160—corrections represented by particular values for a parameters set designated θ. The adjusted abundances are designated $A_t$ and are based on the histogram counts for the associated reference sequences $D_s$ and the corrections represented by values for θ.

Although processes, equipment, and data structures are depicted in FIG. 1A through FIG. 1D as integral blocks in a particular arrangement for purposes of illustration, in other embodiments one or more processes or data structures, or portions thereof, are arranged in a different manner, on the same or different hosts, in one or more databases, or are omitted, or one or more different processes or data structures are included on the same or different hosts.

Thus the clinical data comprises the adjusted counts $A_t$ {t=1, T} of the T reference sequences Q after correction for known systematic errors introduced by the processes 140 and machine 160. Based on the analysis of historical data or other training data, with either baseline (disease free) or known diseased conditions or Known other conditions of interest, or some combination, the presence of a disease or other population differences is known to affect the count of at least one of the reference sequences, t=i but not, or much less, the counts of the other reference sequences t=k≠i. However, variation between runs or processing batches, which has nothing to do with disease state, can confound identification of disease by affecting the count $A_i$.

Of all the reference sequences k≠i not affected by the disease, one or more reference sequences t=j≠i may be known or can be identified in the historical or other training data to be uncorrelated with the disease, whether or not also correlated with the affected reference sequence i absent the disease, and the one or more reference sequences for t=j≠i are called covariates, of which there are one or more in a set indicated by the symbol U with C members. In some embodiments, U is a list that is C elements long of t values associated with the covariates. The abundance of each of the covariate reference sequences is not correlated with the condition of interest. In some embodiments, the covariates do show correlation with the target reference sequence in disease free or baseline cases; but, in other embodiments, the covariates are not correlated with the target reference sequence either. Thus, in some diagnostic methods, the counts of the covariate reference sequences are used to normalize the measurements of the counts of the disease affected reference sequence or sequences. Herein is described a new method to construct an internal control function (also called a normalization function, Y) from the $A_{j1}, ..., A_j, ..., A_{jC}$, for j that is an element of U (j∈U) and j that is not equal to i (j≠i), such that, when $A_i$ is divided by the normalization function Y of the Aj measurements, variations due to run or batch effects are minimized while preserving the signal from a change in DNA copy number, insertions or deletion of sections of DNA associated with disease or population differences.

The normalized abundance of the affected reference sequence i is taken to be the expected abundance in the healthy or standard population, which should be a function of the abundances of the covariates that are not affected by the disease or different population. This can be estimated by the counts of those covariates within the same clinical data. Thus the abundances of the unaffected covariates are called an "internal control" on the estimates of the count $N_i$ of the affected reference sequence i.

Without any loss of generality, the normalization function Y, used as the internal control, is taken to be a weighted linear combination of the covariates, given by Equation 1.1a.

$$Y_i = \Sigma_{j=1}^{C} \delta_j N_j, \ j \in U, \ J \neq i \qquad (1.1a)$$

The normalized clinical measurement $N_i^*$ is then given by Equation 1.1b.

$$N_i^* = A_i \ Y \qquad (1.1b)$$

The values for the $\delta_j$ are selected to minimize the variance of the normalized clinical measurements, $N_i^*$, as given by Equation 1.2.

$$\delta_j = \operatorname{argmin}\{\operatorname{Var} A_i^*\} = \operatorname{argmin}\left\{\operatorname{Var} \frac{A_i}{\Sigma_j \delta_j N_j}\right\}, \qquad (1.2)$$

$$j \in U, \ j \neq i$$

In a current approach, described in an example embodiment below, the values of $\delta_j$ are taken as zero or one ($\delta_j \in 0,1$) and all variances are computed in a brute force approach to find the set of values for $\delta_j$ that minimize the variance. This process can take hours, to days, to weeks of computational time on current devices. This approach was taken because it was not obvious to persons skilled in the art that approximating the variance of the final score could lead to a closed form solution that can be optimized for minimum variance.

In a new approach described herein, it was realized that it was tractable, faster and more accurate to allow the $\delta_j$ to take any real value, positive or negative. In an example embodiment, $\delta_j$ is allowed to be member of the one dimensional real number set, $\mathbb{R}^1$ ($\delta_j \in \mathbb{R}^1$). This realization came about by decomposing the variance of Equation 1.2 as a Taylor series and approximating the variance using only the first order terms, which was not heretofore suggested in the art. The following derivation is provided for purposes of illustration only; and, the embodiments are not limited by the accuracy or completeness of this derivation.

To simplify the notation, let $X=A_i$; and, let $R(X,Y)$ indicate the ratio of X divided by Y that is the value of the normalization function based on the observations. The ratio $R(X,Y)$ is the normalized adjusted count. Furthermore, the relationship between X and Y can be expressed in terms of e1, the remainder when approximating X by Y, as given by Equation 1.3.

$$Y = X + e1 \qquad (1.3)$$

Then $R(X,Y)$ can be defined in terms of a function $R_2(X, e1)$, a function of X and e1, as given by Equation 1.4.

$$R(X,Y) = R_2(X,e1) = X/(X+e1) \qquad (1.4)$$

Then the multidimensional Taylor expansion to first order of approximation is given by Equation 1.5a through 1.5c, where EX is an expected value for the affected reference sequence over many samples in the absence of a count anomaly (e.g., in the absence of a tumor or a disease in the fetus or other change in the sample population; and, x is an actual observed count in the current sample.

$$R_2(x, e1) = \qquad (1.5a)$$
$$R_2(EX, 0) + \frac{\partial R_2(EX, 0)}{\partial x}(x - EX) + \frac{\partial R_2(EX, 0)}{\partial e1}(e1) - e2$$

where e2 is the error in approximation by truncating the Taylor series at the first order.

$$\frac{\partial R_2(EX, 0)}{\partial x} = \left[\frac{1}{x+r} - \frac{x}{(x+e1)^2}\right] \text{ for} \qquad (1.5b)$$
$$(x, e1) = (EX, 0) = \left[\frac{1}{EX} - \frac{EX}{(EX)^2}\right] = 0$$

$$\frac{\partial R_2(EX, 0)}{\partial x} = \left[-\frac{x}{(x+e1)^2}\right] \text{ for} \qquad (1.5c)$$
$$(x, e1) = (EX, 0) = \left[-\frac{EX}{(EX)^2}\right] = -\frac{1}{EX}$$

To evaluate Equations 1.5a and 1.5c, the weights $\delta_j$ are needed. Those weights $\delta_j$ are derived to minimize the variance of $R_2(x, e1)$. The variance of $R_2(x, e1)$ can be written as in Equation 1.6, where the notation Var(R) indicates the variance of the quantity R, the notation E[X] indicates the expected value of X, and Ex is shorthand for E[x]. Thus, ER is shorthand for E[R(x,y)], the expected value of R(x,y).

$$Var(R) = \qquad (1.6)$$
$$E[(R(x, y) - ER)^2] \approx E\left[\left(-\frac{e1}{EX}\right)^2\right] = \frac{E[(e1)^2]}{(EX)^2} = \frac{E[(X-Y)^2]}{(EX)^2}$$

where $E^2X = (EX)^2$. The values of $\delta_j$ that minimize Equation 1.6 for observed values of X (=$A_j$) and $A_j$ can be determined by ordinary least squares (OLS) or related methods, as described in the example embodiment, or by L1 or any other form of linear regression, as well as non-linear optimization, alone or in some combination. The evaluation of the weights is done with the historical data or other training data absent the condition of interest (e.g., for a normal population absent the disease). Typically, a population of at least several hundred samples are included in the trainings data set.

FIG. 2 is a flow chart that illustrates a method for 200 for forming and using internal controls to increase the accuracy and sensitivity of DNA testing, according to an embodiment. Although steps are depicted in FIG. 2 as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways.

In step 201, a target reference sequence (called a target hereinafter for convenience) is determined among the reference sequences to be compared to the sequencing reads. Any method may be used to determine the target. In some embodiments the target is identified in scientific literature as a reference sequence for which the abundance is enhanced or diminished in a condition of interest (called simply a condition hereinafter for convenience), such as aneuploidy in which a whole chromosome is duplicated or absent, or tumors or diseased tissues that express one or more genes or proteins differently from normal cells.

In some embodiments, training data is used; and, the target is identified among the reference sequences by its correlation with the condition of interest known for the samples in the training data. Training data is a set of reference sequence abundances associated with the presence or absence of the condition of interest, among zero or more other conditions, also specified among multiple different subjects. In some embodiments, the training data is obtained by collecting biological samples from multiple subjects known to have the condition of interest or not, and sequencing the samples to determine a reference sequence abundance for all reference sequences for each subject. A reference sequence for which the abundances in the multiple samples are correlated with the occurrence of the condition of interest is then selected as a target reference sequence. As used herein, a subject is any higher order biological organism, including animals such as mammals such as humans.

Any biological sample from the subject that maintains the reference sequence abundances may be used for the training data, or for the clinical samples used in later steps described below. As used herein, biological samples include solid and fluid obtained from a subject. In various embodiments, biological samples may include tissue, organs, cells, protein or membrane extracts of cells, blood or biological fluids such as blood, serum, mucus, urine, ascites fluid or brain fluid (e.g., cerebrospinal fluid, csf).

In step 203, one or more covariate reference sequences (called covariates hereinafter for convenience) are determined. Covariates may be correlated with the target in samples when the condition of interest is absent, but are unaffected, or essentially unaffected (e.g., varying by a few percent or less compared to the target), by, or otherwise uncorrelated with, the occurrence of the condition of interest. For example, in Human prenatal diagnostics, if the test target is chromosome 21 then the counts from the other chromosomes corresponding variability may be under a percent. Any method may be used to determine the covariates. In some embodiments, a covariate is identified in scientific literature as a reference sequence for which the abundance is not substantively enhanced or diminished under condition of interest, but for which the abundance is correlated with the abundance of the target when the condition of interest does not occur. In some embodiments, a covariate is identified among the reference sequences in the training data by its correlation with the target in the absence of the condition of interest but lack of significant correlation with the condition of interest. In some embodiments a covariate is a reference sequence that does not change abundance at all and does not vary even with the target when conditions of interest are absent. In some embodiments, a reference sequence that does vary with occurrence of the condition of interest is selected as a covariate because testing for the covariate is a target region of interest for another test and a normal result for the other test means that the covariate for the region of interest is behaving within accepted parameters.

For example, reference sequences, or regions thereof, which are excluded from use as internal control components are established in some embodiments by omitting regions where any values of the covariates are outside of a critical range. FIG. 2B is a plot 250 that illustrates example distribution of abundances of regions of a chromosome among thousands of samples in a training data. The horizontal axis 252 indicates position along the human chromosomes in number of nucleotides. The vertical axis indicates adjusted abundance $A_t$ of reads aligned with that section. Most sections are found to have adjusted abundances between about 0.8 and 1.2. Sections with variations beyond this are not suitable as covariates. One example of a critical range would be from 0.6 to 1.4. Regions with value outside this range would not be used as covariate reference sequences. For the example depicted in FIG. 2B, positions to exclude are found near positions 15,000,000-17,000,000 bases, 25,000,000 bases, and 42,000,000 bases.

Returning to FIG. 2A, in step 205, a normalization function is defined as a weighted sum of the abundances of the covariates, as given above in Equation 1.1a. It is assumed that there are C such covariates. In some embodiments, the measured target abundance is divided by the normalization function to produce the normalized target abundance. In some embodiments, the target abundance is normalized using a different function of the normalization function e.g., by the product or by dividing by the square of the normalization function.

In step 207, the values of the weights are determined over the one dimensional real numbers, $\mathbb{R}_1$, instead of just over the digital values 0 and 1, to minimize the variance in the normalized count of the target for the data associated with absence of the condition of interest among the data in the training data. By allowing values other than 0 and 1, the brute force determination of the optimal weights to minimize the variance of the normalized count, as taught in previous approaches, is not possible; and thus this approach was not recommended previously. However, here it was determined that the equation to minimize the variance in the normalized counts could be written as a Taylor series and minimized using ordinary least squares or other linear or non-linear techniques. For example, the first order Taylor series of the count for the target divided by the normalization function is defined in Equations 1.5a through 1.5c and its variance given by Equation 1.6 and values for the weights determined by minimizing Equation 1.6 over the training data. In other embodiments, a second or higher order Taylor series is used to determine the functional form of the variance to be minimized. The values of the weights that minimize the variance can be approximated by ordinary least squares (OLS), as described in the example embodiment, or by L1 or any other form of linear regression, polynomial regression, use of the general linear model, logistic regression, mixed models, principal components, partial least squares, weighted least squares, as well as non-linear optimization, alone or in some combination. The evaluation of the weights is done with the historical data or other training data absent the condition of interest (e.g., for a normal population absent the disease).

In steps 209 and 211, the values determined for the weights are used to derive one or more thresholds defining two or more ranges of values for the normalized count of the target which are associated with the condition of interest. In some embodiments, the threshold is determined in a previous step and steps 209 and 211 are omitted. In step 209, normalized target counts are determined for all the cases in the training data by dividing the raw counts of the target by the value of the normalization function based on the weights solved for in step 207 and the counts of the covariates for the same sample in the training data. In step 211, the normalized values are grouped by the rate of occurrence or absence of the condition of interest. It is expected in some embodiments, that a certain range of values is associated with about equal rates of both the occurrence and absence of the condition of interest. This later range can be associated with possible occurrence of the condition of interest. One or more thresholds can be defined to separate the ranges of almost complete absence, from a range with mixed absence and occurrence, from a range with a majority of occurrences, from a range with almost always occurrence.

In steps 213 through 223, each clinical sample (called simply "sample" hereinafter for convenience) is evaluated for the occurrence of the condition of interest, and these steps are repeated for each different clinical sample from the same subject or a different subject. A clinical sample is a biological sample taken from a subject for which it is not known whether the condition of interest occurs.

In step 213, adjusted counts of the reference sequences for the sample are determined, e.g., retrieved from a local or remote data structure such as a database, or derived from measurements obtained directly using a sequencing machine 160, or some combination. The value of the normalizing function is determined based on the weighted sums of the adjusted measured counts of the covariates. The adjusted measured value of the target is then normalized by the value of the normalizing function (e.g., adjusted measured value of the target is divided by the value of the normalizing function). Thus, the normalized target is determined for the clinical sample.

In step 215, it is determined whether the normalized target is beyond a threshold that indicates the conditions of interest occurs, e.g., is below an upper limit (threshold) of a range for the condition of interest, or is above a lower limit (threshold) of a range in which the condition of interest occurs, or some combination. If not, then in step 217 it is determined that the conditions of interest has not occurred in the subject. If so, however, then in step 221 it is determined that the conditions of interest has indeed occurred in the subject, or has possibly occurred in the subject. In step 223, the condition of interest is treated by any method known for the condition of interest.

Using the method 200, a small amount of cells indicative of the condition of interest can be detected in a sample with many cells not in such a condition. Both the sensitivity and accuracy are improved, as will be demonstrated in the following particular embodiments.

2. Example Embodiments

Sehnert et al 2011 and Bianachi et al 2014 describe methods to identify aneuploidy from maternal blood samples, thus avoiding expensive and dangerous invasive procedure; however, they use a normalization functions with weights selected from the values 0 and 1 instead of over the one dimensional real numbers, $\mathbb{R}^1$. In this example, each reference sequences is most or all of an entire chromosome, the condition is Down's syndrome which is indicated by aneuploidy in human chromosome 21 (T21); and thus chromosome 21 is the target. The prior art derivation is repeated here with notation changed to avoid ambiguity with the notation used above. In some embodiments, aneuploidy of a different chromosome, such as 13, 18 or 21, is the condition of interest.

The read sequences q are processed as follows. Reads are aligned to the masked or unmasked Human genome assembly (version hg.19) assembly, which is the entire genome sequence, not just the target region. A read is aligned with a reference sequence at standard criteria (an example would be even with two mismatches provided there are no gaps, and with a read being dropped if it does not align according to this definition, or if it aligns with more than one location on the reference sequence). The number of sites (bases covered by a read alignment to the one reference sequence) in the kth non-overlapping bin of size 100 kilobases (kb, 1 kb=$10^3$ nucleotides) of chromosome t is designated $x_{tk}$. The number of bins in chromosome t is $n_t$. The percentage of G or C nucleotides in the sequence covered by the kth bin of chromosome t is designated $GC_{tk}$. In the example embodiment, the target is a chromosome or a region of a chromosome and the covariates are the chromosomes in a set V of robust chromosomes that includes all chromosomes except common targets 13, 18, 21, x and y, i.e., V={all chromosomes}\{13, 18, 21, x, y}.

Because the fetal fraction is so small, other confounding factors that affect the measured counts of the target are advantageously removed, as described here, to form adjusted counts $A_i$ or $A_j$.

Certain chromosome bins are excluded from further analysis due to observed high variability among baseline (disease free) samples, such that the variability contains little information about aneuploidy state. This was done by manual inspection. Excluded Regions of the Human genome (version hg.19 unmasked) were chromosome y: bases 0-2,000,000; bases 10,000,000-13,000,000; and bases 23,000,000-end of chromosome y.

In addition, corrections are applied for differences in the total number of sequences generated, according to Equation 2.1.

$$nx_{tk} = \frac{x_{tk}}{\sum_{j \in U} \sum_{k=1}^{n_j} x_{tk}} \quad (2.1)$$

Corrections are applied for bin effects according to Equation 2.2.

$$b_{tk} = \frac{nx_{tk}}{\alpha GWP_{tk} + \beta_t} \quad (2.2)$$

where $GWP_{tk}$ is the median of $\{nx_{tk}\}$ over all samples in the training data. In the example embodiment, the training samples included sex chromosomes with female fetuses; but, in other embodiments, other samples are included in the training data. The denominator provides an estimate of the expected count in the bin based on a linear model for expected value of $nx_{tk}$, in which the coefficients $\alpha$ and $\beta'$ (two of the parameters generally referenced above as $\theta$) are determined using a robust Huber-M estimate as implemented in the rim( ) function available from MASS R library at World Wide Web domain r-project in the super domain org hosted at the time of this writing by the Vienna University of Economics and Business, Vienna, Austria.

In Illumina sequencing, coverage is heavily biased by GC content and the resulting bias dominates the small fetal signals of interest. To compensate, a sample-specific GC bias curve is generated in which $b_{tk}$=gcBias($GC_{tk}$) using loess regression on bins from the covariate set V of baseline or disease free training samples, and applied according to Equation 2.3.

$$nb_{tk} = b_{tk} - \quad (2.3)$$
$$\text{Median}\left\{gcBias(GC_{lm}) \forall\, l, m \text{ such that } \left\lfloor \frac{GC_{tk}}{2} \right\rfloor = \left\lfloor \frac{GC_{lm}}{2} \right\rfloor, l \in V\right\}$$

where $\lfloor a \rfloor$ indicates the floor function, which produces the largest integer not greater than the enclosed quantity a. The parameters of gcBias are included among the general parameters $\theta$, for this embodiment.

Confounding maternal sub-chromosomal amplifications and deletions are removed by excluding bins with large deviations from a chromosomal median. To express this correction, the following notation is introduced.

$c_t$=Median($\{nb_{tk}\}$)

$ad_{tk}$=|$nb_{tk}-c_t$|

$MAD_t$=1.4826*Median($ad_{tk}$)

Where $MAD_t$ is the standard deviation of the $ad_{tk}$ when the $nb_{tk}$ are normally distributed.

The final adjusted counts $A_t$ with this correction are then given by Equation 2.4.

$A_t$=Mean($nb_{tm}$) over all m such that $|nb_{tm}-c_t|<3$ $MAD_t$ \quad (2.4)

As stated above, Sehnert et al. (2011) and Biananchi et al. (2014) normalize with weights that are selected from the integers 0 and 1, as described here. The final normalization consists of dividing $A_i$, by an internal control consisting of a linear combination of the $A_j$ from robust set U =V\i. Coefficients of the linear combination are set during training and remain constant for all clinical samples. The normalizing function in this case is a denominator $D_i$ that parallels $Y_i$, described above with reference to Equation 2.4.1a.

The normalized adjusted target counts $B_i$ are associated with occurrence of aneuploidy by defining a z-score called a Normalized Chromosomal Value, NCV, according to Equation 2.5

$$NCV_i = Z_i = \frac{B_i - M_i}{O_i} \quad (2.5)$$

in which $M_i$ is the mean of $B_i$ over all samples from the same flow cell (run batch); and $O_i$ is the standard deviation of $B_i$ over all samples in the training data. The samples strongly associated with aneuploidy fall in one range of the $NCV_i$ ($Z_i$) values of the target i, and those strongly associated with the absence fall in another range, and those strongly with mixed results fall in yet another range. The ranges are separated by thresholds, sometimes called critical values (cr).

When a clinical sample is processed the same way from a subject with unknown conditions, with the now known values of the weights, the condition of the subject can be determined from the value of $NCV_i$ ($Z_i$). For i corresponding to t=13 or 18 or 21 (trisomy chromosome 21 is causative of Down's Syndrome, chromosomes 13 and 18 trisomies are causative of other common congenital genetic defects), the following determinations given by expressions 2.6a through 2.6c were made, based on thresholds in the prior art.

If $Z_i$>$cr_i$ then the subject has aneuploidy of chromosome i \quad (2.6a)

If $ncr_i$<$Z_i$<$cr_i$ then aneuploidy of chromosome i is suspected \quad (2.6b)

If $Z_i$<$ncr_i$ then the subject has a normal number of chromosome i \quad (2.6c)

Where $cr_i$=4.0 and $ncr_i$=2.5 for i corresponding to t=13 or 18 or 21. Estimates are similarly defined for aneuploidy involving sex chromosomes x and y.

Using the methods described above, e.g, with reference to FIG. 2, the $\delta_j$ are evaluated over the real numbers, and the variance is further minimized, yielding other values for the NCV, and, in some embodiments, different ranges and thresholds, all in less time. At the same time, the decreased variance provides greater sensitivity and accuracy. For example, in the Table 1, 40 normal pregnancy samples are processed and use of regression coefficients results in an approximately 50% reduction in variance, leading to greater sensitivity and specificity to distinguish disorders in low fetal fraction samples.

TABLE 1

Comparison of Var(R) values between different methods to determine $\delta_j$.

| Test Target Region | $\delta_j \in \{0, 1\}$ | $\delta_j$ by Regression Coefficients |
|---|---|---|
| Chromosome 13 | 0.0015 | 0.00103 |
| Chromosome 18 | 0.0016 | 0.00073 |
| Chromosome 21 | 0.0019 | 0.000862 |

In various embodiments, any method of identifying commonly occurring copy number variations can be used. For example, taking the loci removed from calculation in formula 2.4 above. Additionally, internal control components (covariates) can be selected from common copy number regions, which are first tested for aneuploidy. One way of implementing this is to select regions of chromosome 21 Downs syndrome critical region in Human prenatal testing. A first test for trisomy 21 will tell if this region has large scale aneuploidy before relying on loci from the region as internal control component.

3. Hardware Overview

Figure 3:
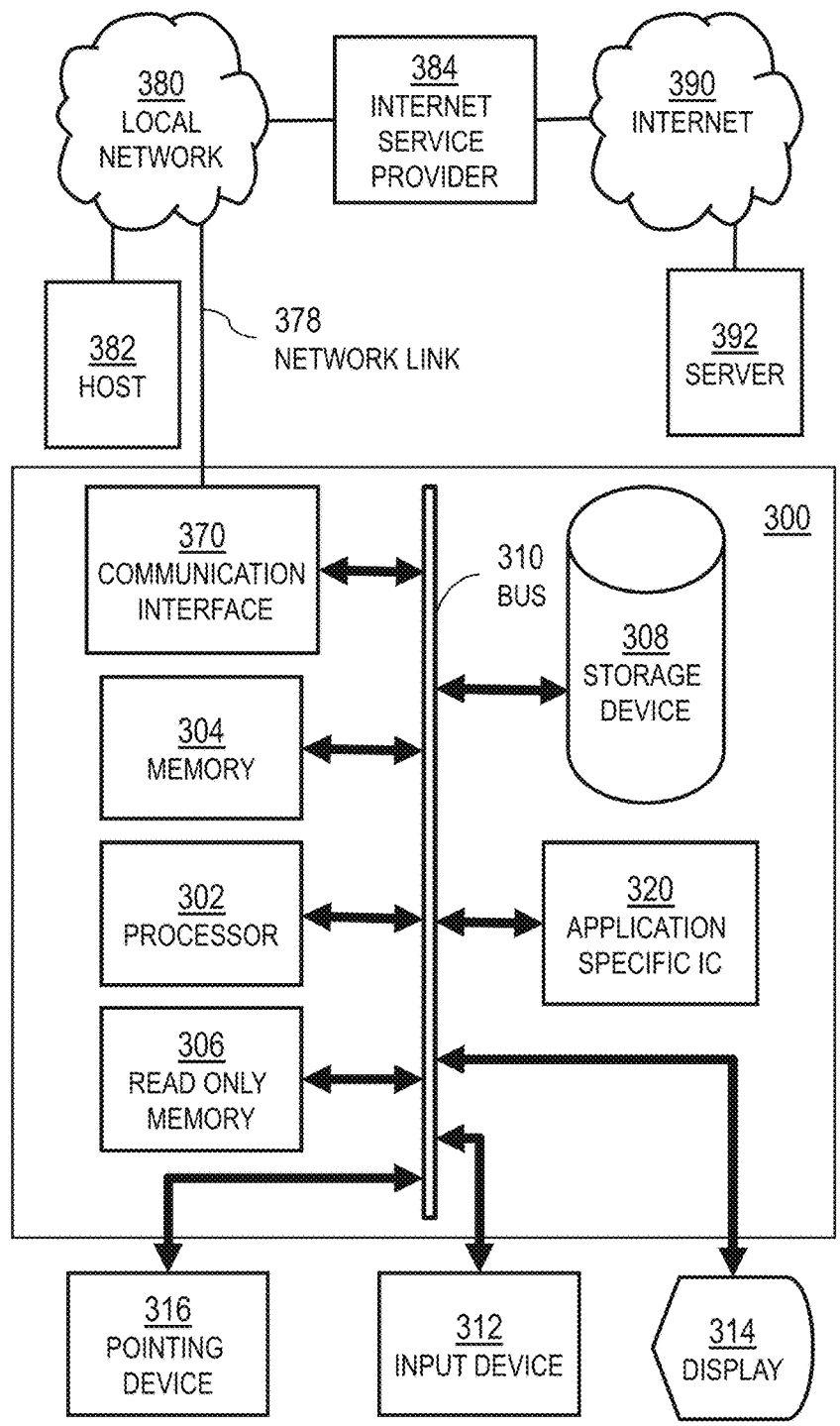
FIG. 3 is a block diagram that illustrates a computer system upon which an embodiment of the invention may be implemented.

FIG. 3 is a block diagram that illustrates a computer system 300 upon which an embodiment of the invention may be implemented. Computer system 300 includes a communication mechanism such as a bus 310 for passing information between other internal and external components of the computer system 300. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit).). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 300, or a portion thereof, constitutes a means for performing one or more steps of one or more methods described herein.

A sequence of binary digits constitutes digital data that is used to represent a number or code for a character. A bus 310 includes many parallel conductors of information so that information is transferred quickly among devices coupled to the bus 310. One or more processors 302 for processing information are coupled with the bus 310. A processor 302 performs a set of operations on information. The set of operations include bringing information in from the bus 310 and placing information on the bus 310. The set of operations also typically include comparing two or more units of information, shifting positions of units of information, and combining two or more units of information, such as by addition or multiplication. A sequence of operations to be executed by the processor 302 constitute computer instructions.

Computer system 300 also includes a memory 304 coupled to bus 310. The memory 304, such as a random access memory (RAM) or other dynamic storage device, stores information including computer instructions. Dynamic memory allows information stored therein to be changed by the computer system 300. RAM allows a unit of information stored at a location called a memory address to be stored and retrieved independently of information at neighboring addresses. The memory 304 is also used by the processor 302 to store temporary values during execution of computer instructions. The computer system 300 also includes a read only memory (ROM) 306 or other static storage device coupled to the bus 310 for storing static information, including instructions, that is not changed by the computer system 300. Also coupled to bus 310 is a non-volatile (persistent) storage device 308, such as a magnetic disk or optical disk, for storing information, including instructions, that persists even when the computer system 300 is turned off or otherwise loses power.

Information, including instructions, is provided to the bus 310 for use by the processor from an external input device 312, such as a keyboard containing alphanumeric keys operated by a human user, or a sensor. A sensor detects conditions in its vicinity and transforms those detections into signals compatible with the signals used to represent information in computer system 300. Other external devices coupled to bus 310, used primarily for interacting with humans, include a display device 314, such as a cathode ray tube (CRT) or a liquid crystal display (LCD), for presenting images, and a pointing device 316, such as a mouse or a trackball or cursor direction keys, for controlling a position of a small cursor image presented on the display 314 and issuing commands associated with graphical elements presented on the display 314.

In the illustrated embodiment, special purpose hardware, such as an application specific integrated circuit (IC) 320, is coupled to bus 310. The special purpose hardware is configured to perform operations not performed by processor 302 quickly enough for special purposes. Examples of application specific ICs include graphics accelerator cards for generating images for display 314, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 300 also includes one or more instances of a communications interface 370 coupled to bus 310. Communication interface 370 provides a two-way communication coupling to a variety of external devices that operate with their own processors, such as printers, scanners and external disks. In general the coupling is with a network link 378 that is connected to a local network 380 to which a variety of external devices with their own processors are connected. For example, communication interface 370 may be a parallel port or a serial port or a universal serial bus (USB) port on a personal computer. In some embodiments, communications interface 370 is an integrated services digital network (ISDN) card or a digital subscriber line (DSL) card or a telephone modem that provides an information communication connection to a corresponding type of telephone line. In some embodiments, a communication interface 370 is a cable modem that converts signals on bus 310 into signals for a communication connection over a coaxial cable or into optical signals for a communication connection over a fiber optic cable. As another example, communications interface 370 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 370 sends and receives electrical, acoustic or electromagnetic signals, including infrared and optical signals, that carry information streams, such as digital data.

The term computer-readable medium is used herein to refer to any medium that participates in providing information to processor 302, including instructions for execution. Such a medium may take many forms, including, but not limited to, non-volatile media, volatile media and transmission media. Non-volatile media include, for example, optical or magnetic disks, such as storage device 308. Volatile media include, for example, dynamic memory 304. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 302, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 302, except for carrier waves and other signals.

Logic encoded in one or more tangible media includes one or both of processor instructions on a computer-readable storage media and special purpose hardware, such as ASIC 320.

Network link 378 typically provides information communication through one or more networks to other devices that use or process the information. For example, network link 378 may provide a connection through local network 380 to a host computer 382 or to equipment 384 operated by an Internet Service Provider (ISP). ISP equipment 384 in turn provides data communication services through the public, world-wide packet-switching communication network of networks now commonly referred to as the Internet 390. A computer called a server 392 connected to the Internet provides a service in response to information received over the Internet. For example, server 392 provides information representing video data for presentation at display 314.

The invention is related to the use of computer system 300 for implementing the techniques described herein. According to one embodiment of the invention, those techniques are performed by computer system 300 in response to processor 302 executing one or more sequences of one or more instructions contained in memory 304. Such instructions, also called software and program code, may be read into memory 304 from another computer-readable medium such as storage device 308. Execution of the sequences of instructions contained in memory 304 causes processor 302 to perform the method steps described herein. In alternative embodiments, hardware, such as application specific integrated circuit 320, may be used in place of or in combination with software to implement the invention. Thus, embodiments of the invention are not limited to any specific combination of hardware and software.

The signals transmitted over network link 378 and other networks through communications interface 370, carry information to and from computer system 300. Computer system 300 can send and receive information, including program code, through the networks 380, 390 among others, through network link 378 and communications interface 370. In an example using the Internet 390, a server 392 transmits program code for a particular application, requested by a message sent from computer 300, through Internet 390, ISP equipment 384, local network 380 and communications interface 370. The received code may be executed by processor 302 as it is received, or may be stored in storage device 308 or other non-volatile storage for later execution, or both. In this manner, computer system 300 may obtain application program code in the form of a signal on a carrier wave.

Various forms of computer readable media may be involved in carrying one or more sequence of instructions or data or both to processor 302 for execution. For example, instructions and data may initially be carried on a magnetic disk of a remote computer such as host 382. The remote computer loads the instructions and data into its dynamic memory and sends the instructions and data over a telephone line using a modem. A modem local to the computer system 300 receives the instructions and data on a telephone line and uses an infra-red transmitter to convert the instructions and data to a signal on an infra-red a carrier wave serving as the network link 378. An infrared detector serving as communications interface 370 receives the instructions and data carried in the infrared signal and places information representing the instructions and data onto bus 310. Bus 310 carries the information to memory 304 from which processor 302 retrieves and executes the instructions using some of the data sent with the instructions. The instructions and data received in memory 304 may optionally be stored on storage device 308, either before or after execution by the processor 302.

Figure 4:
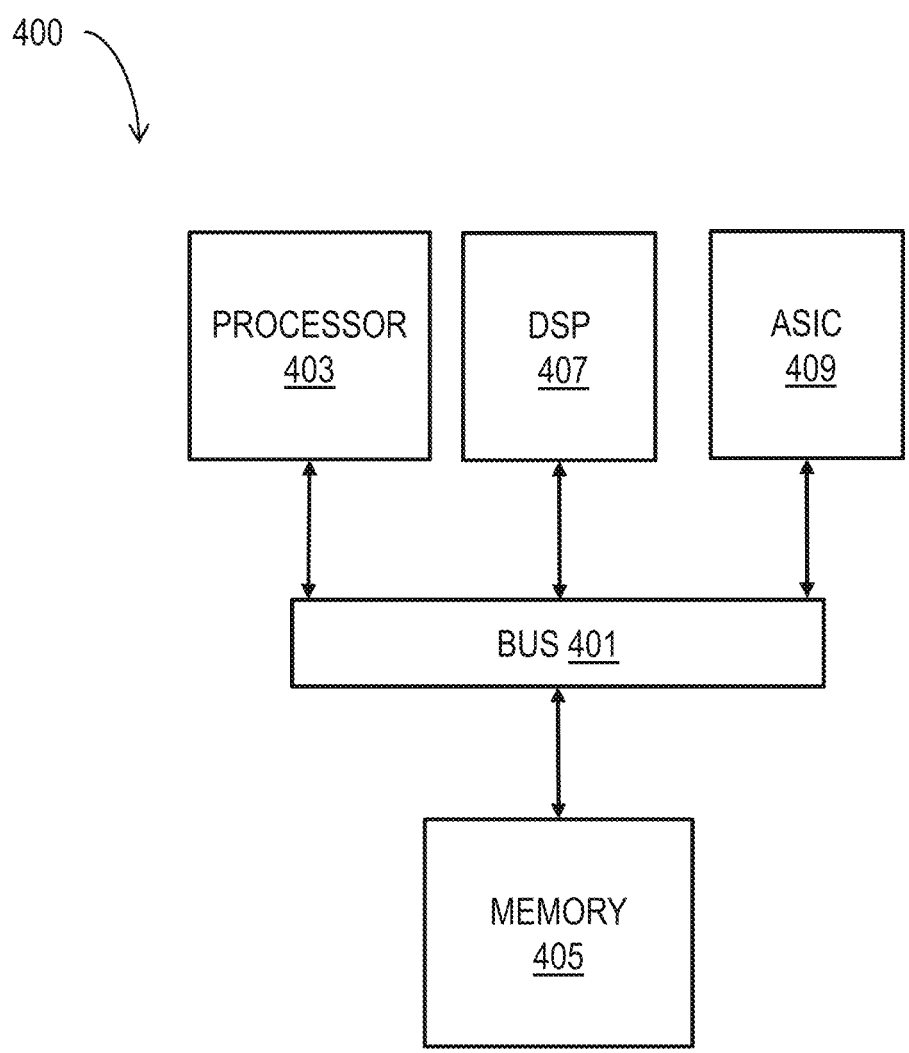
FIG. 4 is a block diagram that illustrates a chip set upon which an embodiment of the invention may be implemented.

FIG. 4 illustrates a chip set 400 upon which an embodiment of the invention may be implemented. Chip set 400 is programmed to perform one or more steps of a method described herein and includes, for instance, the processor and memory components described with respect to FIG. 3 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 400, or a portion thereof, constitutes a means for performing one or more steps of a method described herein.

In one embodiment, the chip set 400 includes a communication mechanism such as a bus 401 for passing information among the components of the chip set 400. A processor 403 has connectivity to the bus 401 to execute instructions and process information stored in, for example, a memory 405. The processor 403 may include one or more processing cores with each core configured to perform independently. A multi-core processor enables multiprocessing within a single physical package. Examples of a multi-core processor include two, four, eight, or greater numbers of processing cores. Alternatively or in addition, the processor 403 may include one or more microprocessors configured in tandem via the bus 401 to enable independent execution of instructions, pipelining, and multithreading. The processor 403 may also be accompanied with one or more specialized components to perform certain processing functions and tasks such as one or more digital signal processors (DSP) 407, or one or more application-specific integrated circuits (ASIC) 409. A DSP 407 typically is configured to process real-world signals (e.g., sound) in real time independently of the processor 403. Similarly, an ASIC 409 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 403 and accompanying components have connectivity to the memory 405 via the bus 401. The memory 405 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 405 also stores the data associated with or generated by the execution of one or more steps of the methods described herein.

4. Alternations, Extensions And Modifications

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items, elements or steps. Furthermore, the indefinite article "a" or "an" is meant to indicate one or more of the item, element or step modified by the article. As used herein, unless otherwise clear from the context, a value is "about" another value if it is within a factor of two (twice or half) of the other value. While example ranges are given, unless otherwise clear from the context, any contained ranges are also intended in various embodiments. Thus, a range from 0 to 10 includes the range 1 to 4 in some embodiments.

5. REFERENCES

Sehnert et al. 2011 Clinical Chemistry 57(7):1042-1049.
Biananchi et al. 2014 N Engl J Med 370(9):799-808.

What is claimed is:

1. A method for sampling with a massively parallel sequencing machine comprising:
obtaining on a processor first data that indicates a measured amount of each of a plurality of reference sequences for nucleic acids from each of a plurality of training samples, wherein the plurality of reference sequences includes
a target reference sequence for which a relative abundance compared to other reference sequences is indicative of a condition of interest, and
a set of one or more covariate reference sequences different from the target reference sequence, wherein a relative abundance of each of the covariate reference sequences is not correlated with the condition of interest;
determining automatically on a processor a value over real numbers for each weight of a set of one or more weights for a normalization function that involves a sum of relative abundances of the set of one or more covariate reference sequences, each relative abundance multiplied by a corresponding one of the set of one or more weights, based on minimizing a variance of a Taylor expansion of a ratio of a measured amount of the target reference sequence divided by a value of the normalization function evaluated with measured amounts of the set of one or more covariate reference sequences over a portion of the first data in which the condition of interest does not occur;
obtaining on a processor second data that indicates a measured amount of the target reference sequence and a measured amount of each of the covariate reference sequences in a clinical sample from a subject and;
reducing variance of a measurement of the target reference sequence by determining automatically on a processor a normalized target value equal to a ratio of the measured amount of the target reference sequence in the second data divided by a value of the normalization function evaluated with measured amounts of the set of one or more covariate reference sequences over the second data.

2. The method as recited in claim 1, further comprising: determining that the condition of interest has occurred in the subject based on the normalized target value being beyond a threshold value.

3. The method as recited in claim 2, further comprising, before determining that the condition of interest has occurred, determining automatically on a processor the threshold value based on a plurality of normalized target values, each equal to a ratio of the measured amount of the target reference sequence in one instance of the first data divided by a value of the normalization function evaluated with measured amounts of the set of one or more covariate reference sequences in the instance of the first data.

4. The method as recited in claim 2, wherein there is a treatment for the condition of interest, and the method further comprises treating the subject when it is determined that the condition of interest has occurred.

5. The method as recited in claim 2, wherein: the clinical sample includes a component from blood of a pregnant female mammalian subject; each different reference sequence is a different entire chromosome of a species of the subject; and the condition of interest is aneuploidy in a fetus carried by the subject.

6. The method as recited in claim 2, wherein the condition of interest is cancer.

7. The method as recited in claim 1, further comprising, before determining the value over real numbers for each weight, determining automatically on a processor the target reference sequence based on the first data.

8. The method as recited in claim 1, further comprising, before determining the value over real numbers for each weight, determining automatically on a processor, the set of one or more covariate reference sequences.

9. The method as recited in claim 1, further comprising, before said operating the massively parallel sequencing machine on the clinical sample, drawing the clinical sample from the subject.

10. The method as recited in claim 1, wherein said determining automatically on the processor the value over real numbers for each weight of the set of one or more weights is accomplished in about one day or less.

11. A non-transitory computer-readable medium carrying one or more sequences of instructions, wherein execution of the one or more sequences of instructions by one or more processors causes an apparatus to perform the steps of:
obtaining first data that indicates a measured amount of each of a plurality of reference sequences for nucleic acids from each of a plurality of training samples, wherein the plurality of reference sequences includes
a target reference sequence for which a relative abundance compared to other reference sequences is indicative of a condition of interest, and
a set of one or more covariate reference sequences different from the target reference sequence, wherein a relative abundance of each of the covariate reference sequences is not correlated with the condition of interest;
determining a value over real numbers for each weight of a set of one or more weights for a normalization function that involves a sum of relative abundances of the set of one or more covariate reference sequences, each relative abundance multiplied by a corresponding one of the set of one or more weights, based on minimizing a variance of a Taylor expansion of a ratio of a measured amount of the target reference sequence divided by a value of the normalization function evaluated with measured amounts of the set of one or more covariate reference sequences over a portion of the first data in which the condition of interest does not occur:
obtaining second data that indicates a measured amount from a massively parallel sequencing machine for both the target reference sequence and each of the covariate reference sequences in a clinical sample from a subject: and
determining a normalized target value equal to a ratio of the measured amount of the target reference sequence in the second data divided by a value of the normalization function evaluated with measured amounts of the set of one or more covariate reference sequences over the second data.

12. A non-transitory computer-readable medium as recited in claim 11, wherein the apparatus is further caused to:
determine that the condition of interest has occurred in the subject if the normalized target value is beyond a threshold value.

13. A non-transitory computer-readable medium as recited in claim 12, wherein: the clinical sample includes a component from blood of a pregnant female mammalian subject; each different reference sequence is a different entire chromosome of a species of the subject; and the condition of interest is aneuploidy in a fetus carried by the subject.

14. The non-transitory computer-readable medium as recited in claim 12, wherein the condition of interest is cancer.

15. A non-transitory computer-readable medium as recited in claim 11, wherein said determining the value over real numbers for each weight of the set of one or more weights is accomplished in about one day or less.

16. A system comprising:
a massively parallel sequencing machine:
at least one processor; and
at least one memory including one or more sequences of instructions,
the at least one memory and the one or more sequences of instructions configured to, with the at least one processor, cause an apparatus to perform at least the following,
obtain first data that indicates a measured amount of each of a plurality of reference sequences for nucleic acids from each of a plurality of training samples, wherein the plurality of reference sequences includes
a target reference sequence for which a relative abundance compared to other reference sequences is indicative of a condition of interest, and
a set of one or more covariate reference sequences different from the target reference sequence, wherein a relative abundance of each of the covariate reference sequences is not correlated with the condition of interest;
determine a value over real numbers for each weight of a set of one or more weights for a normalization function that involves a sum of relative abundances of the set of one or more covariate reference sequences, each relative abundance multiplied by a corresponding one of the set of one or more weights, based on minimizing a variance of a Taylor expansion of a ratio of a measured amount of the target reference sequence divided by a value of the normalization function evaluated with measured amounts of the set of one or more covariate reference sequences over a portion of the first data, in which the condition of interest does not occur;
obtain second data that indicates a measured amount from a massively parallel sequencing machine for both the target reference sequence and each of the covariate reference sequences in a clinical sample from a subject; and
determine a normalized target value equal to a ratio of the measured amount of the target reference sequence in the second data divided by a value of the normalization function evaluated with measured amounts of the set of one or more covariate reference sequences over the second data.

17. A system as recited in claim 16, wherein the apparatus is further caused to:
determine that the condition of interest has occurred in the subject if the normalized target value is beyond a threshold value.

18. A system as recited in claim 17, wherein: the clinical sample includes a component from blood of a pregnant female mammalian subject; each different reference sequence is a different entire chromosome of a species of the subject; and the condition of interest is aneuploidy in a fetus carried by the subject.

19. The system as recited in claim 17, wherein the condition of interest is cancer.

20. A system as recited in claim 16, wherein said determining the value over real numbers for each weight of the set of one or more weights is accomplished in about one day or less.

21. An apparatus comprising:
means for obtaining first data that indicates a measured amount of each of a plurality of reference sequences for nucleic acids from each of a plurality of training samples, wherein the plurality of reference sequences includes
a target reference sequence for which a relative abundance compared to other reference sequences is indicative of a condition of interest, and a set of one or more covariate reference sequences different from the target reference sequence, wherein a relative abundance of each of the covariate reference sequences is not correlated with the condition of interest; and means for determining a value over real numbers for each weight of a set of one or more weights for a normalization function that involves a sum of relative abundances of the set of one or more covariate reference sequences, each relative abundance multiplied by a corresponding one of the set of one or more weights, based on minimizing a variance of a Taylor expansion of a ratio of a measured amount of the target reference sequence divided by a value of the normalization function evaluated with measured amounts of the set of one or more covariate reference sequences over a portion of the first data in which the condition of interest does not occur means for obtaining second data that indicates a measured amount of the target reference sequence and a measured amount of each of the covariate reference sequences in a clinical sample from a subject; and means for determining a normalized target value equal to a ratio of the measured amount of the target reference sequence in the second data divided by a value of the normalization function evaluated with measured amounts of the set of one or more covariate reference sequences over the second data.

22. An apparatus as recited in claim 21, further comprising:

means for determining that the condition of interest has occurred in the subject based on the normalized target value being beyond a threshold value.

23. An apparatus as recited in claim 22, wherein: the clinical sample includes a component from blood of a pregnant female mammalian subject; each different reference sequence is a different entire chromosome of a species of the subject; and the condition of interest is aneuploidy in a fetus carried by the subject.

24. The apparatus as recited in claim 22, wherein the condition of interest is cancer.

25. An apparatus as recited in claim 21, wherein said determining the value over real numbers for each weight of the set of one or more weights is accomplished in about one day or less.

* * * * *